United States Patent [19]

Serafini et al.

[11] 4,244,857
[45] Jan. 13, 1981

[54] CURING AGENT FOR POLYEPOXIDES AND EPOXY RESINS AND COMPOSITES CURED THEREWITH

[75] Inventors: Tito T. Serafini, Middleburg Hts.; Peter Delvigs, Fairview Park; Raymond D. Vannucci, Brooklyn, all of Ohio

[73] Assignee: The United States of America as represented by the Administrator of the National Aeronautics and Space Administration, Washington, D.C.

[21] Appl. No.: 70,771

[22] Filed: Aug. 30, 1979

[51] Int. Cl.³ .................. C08K 7/06; C08G 59/02; C07D 207/06
[52] U.S. Cl. .................. 260/37 EP; 260/326 S; 260/326 N; 528/117; 528/118; 528/322
[58] Field of Search .......... 260/326 N, 326 S, 37 EP; 528/403, 117, 118, 322

[56] References Cited

U.S. PATENT DOCUMENTS

| | | | |
|---|---|---|---|
| 3,838,101 | 9/1974 | Steele et al. | 528/117 |
| 3,897,395 | 7/1975 | D'Alelio | 260/326 N |
| 3,917,643 | 11/1975 | Takekoshi et al. | 260/326 N |
| 4,066,631 | 1/1977 | Dimmig | 528/322 |
| 4,092,297 | 5/1978 | Williams | 528/322 |

FOREIGN PATENT DOCUMENTS 49-35079  9/1974  Japan ........................ 528/117
1069061  5/1967  United Kingdom ............... 260/326 N

*Primary Examiner*—V. P. Hoke
*Attorney, Agent, or Firm*—Norman T. Musial; John R. Manning; James A. Mackin

[57] ABSTRACT

A curing agent for a polyepoxide has the formula:

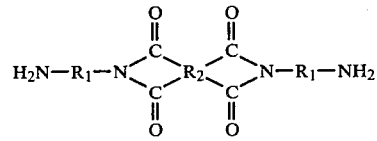

wherein $R_1$ is a divalent aryl radical such as phenylene and wherein $R_2$ is a tetravalent aryl radical such as a tetravalent benzene radical. An epoxide is cured by admixture with the curing agent. The cured epoxy product retains the usual properties of cured epoxides and, in addition, has a high char residue after burning, on the order of 45% by weight. The high char residue is of value in preventing release to the atmosphere of carbon fibers from carbon fiber-epoxy resin composites in the event of burning of the composite.

5 Claims, No Drawings

CURING AGENT FOR POLYEPOXIDES AND EPOXY RESINS AND COMPOSITES CURED THEREWITH

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

This invention relates to curing agents for polyepoxides. In one aspect, the invention relates to the curing agents and to methods of making same. In another aspect, the invention relates to cured epoxy resins and to methods of curing polyepoxides using novel curing agents in accordance with the invention. In another aspect, the invention relates to carbon fiber-epoxy resin composites in which the epoxy resin is cured with novel curing agents of the invention.

Epoxy resins form a well known class of resins having outstanding properties for many uses. The resins are made by curing a polyepoxide with a curing agent. Many types of polyepoxides and curing agents are known and are fully described in the literature. While the presently available materials are excellent in their field of use, it is generally advantageous to discover new materials which are useful as alternatives to those presently available provided, of course, that the generally excellent properties of the epoxy resins are retained.

Epoxy resins are widely used in composite materials in which fibers of glass, carbon, and so forth, are impregnated with an epoxy resin system (i.e. a polyepoxide and a curing agent) followed by curing to form the composite product. When carbon fibers are used, one difficulty has arisen in that, if the composite is burned, several of the carbon fibers may be released to the environment and such release can be troublesome. In this regard, it will be noted that carbon fibers are electrically conductive and released fibers may short-circuit or otherwise interfere with electrical components with which it comes in contact.

It is an object of the invention to provide a novel curing agent for polyepoxides. It is a further object to provide a method of curing polyepoxides using a novel curing agent and to provide cured epoxy resins cured therewith. It is still a further object to provide carbon fiber-epoxy resin composites which, upon burning, form a high amount of char which will serve to decrease the release of carbon fibers to the atmosphere.

BRIEF SUMMARY OF THE INVENTION

The foregoing and other objects which will be apparent to those having ordinary skill in the art are achieved in accordance with the present invention by providing a novel aromatic bis (amino-imide) curing agent for polyepoxides, the curing agent having the formula:

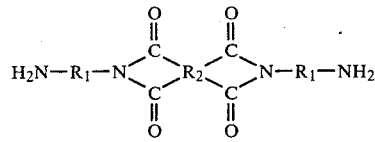

wherein $R_1$ is a divalent aryl radical and $R_2$ is a tetravalent aryl radical. The curing agents may be made by reacting a diamine having the formula:

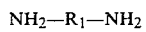

with a member selected from the group consisting of anhydrides having the formula:

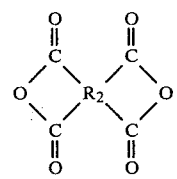

and diester-diacids of said anhydride having the formula:

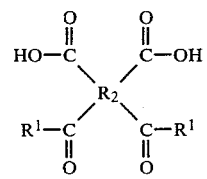

wherein $R_1$ is an alkyl radical.

Polyepoxides may be cured by reaction with these novel curing agents and the cured polyepoxides, which yield a high char on burning, may be used to make carbon fiber-epoxy resin composites.

DETAILED DESCRIPTION

The polyepoxides to which the invention relates are widely known and described in the literature and need not be redescribed here.

The curing agent in accordance with the invention is an aromatic bis (amino-imide) which is capable of providing cured epoxy resins having a high char on burning while at the same time retaining the outstanding characteristics and mechanical properties that are widely recognized for epoxy resins. The curing agent has the formula:

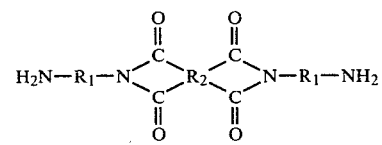

wherein $R_1$ is a divalent aryl radical and $R_2$ is a tetravalent aryl radical. The curing agents are conveniently prepared by reacting a diamine having the formula:

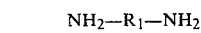

with an anhydride having the formula:

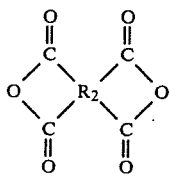

or a diacid-diester thereof having the formula:

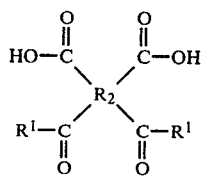

wherein $R_1$ is an alkyl radical, preferably $C_1$ to $C_4$.

Examples of diamines include those in which $R_1$ is a radical having the formula:

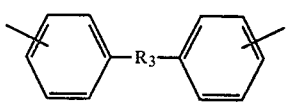

wherein $R_3$ is a divalent radical such as $CH_2$, $O$, $SO_2$, and those in which $R_1$ is phenylene. Representative examples include 4,4'-methylenedianiline, 4,4-oxydianiline, 4,4-sulfonyldianiline, p-phenylenediamine, m-phenylenediamine.

Examples of anhydrides include those in which $R_2$ is a tetravalent aryl radical such as a tetravalent benzene radical or a radical having the formula:

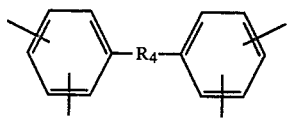

wherein $R_4$ is a divalent radical such as $CF_3$—C—$CF_3$, $SO_2$, $CO$, and $O$.

The ratio of the diamine to the dianhydride is preferably about stoichiometric (2:1) and is preferably conducted in a suitable solvent such as N, N-dimethylformamide, N, N-dimethylacetamide or N-methylpyrrolidone. The resulting bis (amino-imides) are isolated as solids and are employed as curing agents for epoxy resins. The mixtures of epoxy resins and curing agent are used to impregnate fibers, such as carbon or glass, and are also filled with particulate fillers to provide high performance fiber reinforced plastic articles or filled epoxy resins which are used to fabricate a wide variety of molded articles.

The cured epoxy resins have a char of about 45% on burning compared with about 25% on burning epoxy resins made with conventional curing agents. This extra body of char serves to retain, in carbon fiber-epoxy composites, embedded carbon fibers, thus reducing the amount of carbon fibers which could otherwise be released to the atomosphere.

Several examples of the invention, including preferred embodiments, follow.

EXAMPLE 1

A solution of 8.88 g of 4,4'-(hexafluoroisopropylidene)-bis (phthalic anhydride) in 26.64 g of anhydrous N-methyl pyrrolidone is added dropwise at room temperature to a stirred solution of 7.92 g of 4,4'-methylenedianiline in 23.76 g of anhydrous N-methyl pyrrolidone under a nitrogen atmosphere. After the addition is completed, the solution is stirred at room temperature under nitrogen for 2 hours. The solution is then heated under reflux for 2 hours. After cooling, the solution is poured into 400 ml of water with vigorous stirring. The precipitate is filtered, washed with water, and dried under vacuum at 100° C. to yield 15-16 g of the bisaminoimide, m.p. 165°-175° C.

EXAMPLE 2

A suspension of 17.76 g of 4,4'-(hexafluoroisopropylidene)-bis (phthalic anhydride) in 6.77 of anhydrous methanol is heated under reflux until the solid dissolves, then for an additional 2 hours. The excess solvent is evaporated under reduced pressure in a rotary evaporator. Next, 15.84 g of 4,4'-methylenedianiline and 12 g of N-methylpyrrolidone are added to the reaction flask. The resulting solution is heated under reflux for 2 hours. After cooling, the solution is poured into 100 ml of water with vigorous stirring. The precipitate is filtered, washed with water, and dried under vacuum at 100° C. to yield 15.5-16 g of the bisaminoimide, m.p. 145°-160°.

EXAMPLE 3

A mixture of 10 g of N,N,N', N'-tetraglycidyl methylene dianiline (epoxide equivalent weight=125) and 16.1 g of the bisaminoimide prepared in Example 2 from 4,4'-methylene dianiline and 4,4'-(hexafluoroisopropylidene)- bis (phthalic anhydride) (amine hydrogen equivalent=201) is dissolved in 26 g of methyl ethyl ketone by first placing the epoxide into solution at room temperature and then adding the amine hardener slowly with stirring and gentle heating (below 50° C.). The solids dissolved within 30 minutes.

Approximately 38 g of graphite fiber are impregnated with the above solution by first winding the graphite fiber onto a mandrel, then applying the solution evenly to the fiber with a brush. The impregnated fiber is then dried at 50° C. for 1 hour on the mandrel and then 24 hours at room temperature to reduce the solvent content. The impregnated material at this point is easily cut and shaped into various forms.

Twelve plies of the impregnated fiber, 3 by 7-15/16 inches, are cut and then stacked into a 3 by 8 inch mold at room temperature. The mold temperture is then increased at 8° C./min. to 110° C. and then 15 psi pressure is applied. After 15 minutes at 15 psi and 110° C., the pressure is maintained and the temperature is increased at 3° C./min. through the resin gelation temperature of 155° C., at which temperature a pressure of 120 psi is applied. Heating and pressure are continued to the final cure temperature of 177° C. After 120 minutes at 177° C. and 120 psi, the mold temperature is reduced to 100° C., the pressure released and the composite removed.

The resulting composite is essentially void-free and exhibits excellent mechanical properties, such as room temperature and 177° C. flexural strengths of $224 \times 10^3$ psi and $106 \times 10^3$ psi, respectively, after a post-cure of 24 hours in air at 204° C.

EXAMPLE 4

A mixture of 13 g of N,N,N'N'-tetraglycidyl methylene dianiline (epoxide equivalent weight=125), 3.90 g of 4,4'-methylene dianiline (amine hydrogen equivalent weight=49.5), and 5.23 g of the bisaminoimide prepared in Example 2 from 4,4'-methylenedianiline and 4,4'-(hexefluoroisopropylidene)- bis (phthalic anhydride) (amine hydrogen equivalent=201) is dissolved in 23 g of methyl ethyl ketone by first placing the epoxide into solution at room temperature and then adding the amine hardeners slowly with stirring and gentle heating (below 50° C.). The amine solids dissolved within 30 minutes.

Approximately 32 g of graphite fiber are impregnated with the above solution by first winding the graphite fiber onto a mandrel, then applying the solution evenly to the fiber with a brush. The impregnated fiber is then dried at 50° C. for 15 minutes on the mandrel and then 24 hours at room temperature. The impregnated material at this point is easily cut and shaped into various forms.

The impregnated fiber is then cut into twelve 3 by 7-15/16 inch plies and stacked in a 3×8 inch mold at room temperature. The mold temperature is then increased at 8° C./min. to 110° C. and 15 psi pressure is applied. After 30 minutes at 110° C. and 15 psi, the pressure is increased to 120 psi and the temperature increased to 177° C. After 120 minutes at 177° C. and 120 psi, the mold temperature is reduced to 100° C., the pressure released and the composite removed.

The resulting composite is essentially void-free and exhibits excellent mechanical properties, such as room temperature and 177° C. flexural strength of $209 \times 10^3$ psi and $106 \times 10^3$ psi, respectively, after a post-cure of 24 hours in air at 204° C.

EXAMPLE 5

The procedure of Example 1 is followed, using a solution of 8.88 g of 4,4'-(hexafluoroisopropylidene)-bis (phthalic anhydride) in 26.64 g of N-methylpyrrolidone (NMP) and a solution of 9.92 g of 4,4'-sulfonyldiamiline (DDS) in 29.76 g of NMP to synthesize the bis (amino-imide) from 4,4'-(hexafluoroisopropylidine)-bis (phthalic anhydride) (6F) and DDS.

EXAMPLE 6

The procedure of Example 1 is followed to synthesize the bis amino imide from 6F and 4,4'-oxydiamiline (ODA), using a solution of 8.88 g of 6F in 26.64 g of NMP and a solution of 8.00 g of ODA in 24.00 g of NMP.

EXAMPLE 7

The procedure of Example 1 is followed to synthesize the bis amino imide from 6F and p-phenylenediamine (PPDA), using a solution of 8.88 g of 6F in 26.64 g of NMP, and a solution of 4.32 g of PPDA in 12.96 g of NMP.

EXAMPLE 8

The procedure of Example 1 is followed to synthesize the bis amino imide from 6F and m-phenylenediamine (MPDA), using a solution of 8.88 g of 6F in 26.64 g of NMP, and a solution of 4.32 g of MPDA in 12.96 g of NMP.

EXAMPLE 9

Using the bis amino imide from Example 5 and the procedure from Example 3, composites are prepared which exhibit properties comparable to those of Example 3.

EXAMPLE 10

Using the bis amino imide from Example 6 and the procedure from Example 3, composites are prepared which exhibit properties comparable to those of Example 3.

EXAMPLE 11

Example 9 is followed, with comparable results, except bis amino imide from Example 7 is used.

EXAMPLE 12

Example 9 is followed, with comparable results, except bis amino imide from Example 8 is used.

EXAMPLE 13

Example 4 is followed with the bis amino imides prepared in Examples 5, 6, 7 and 8 and the parent diamine. Results are comparable to those of Example 4.

What is claimed is:

1. An aromatic bis (amino-imide) having the formula:

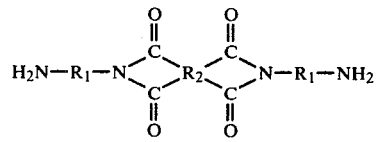

wherein $R_1$ is a divalent aryl radical having the formula:

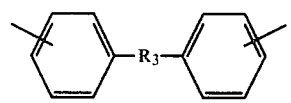

wherein $R_3$ is selected from the group consisting of $CH_2$, O, and $SO_2$, and $R_2$ is a tetravalent aryl radical having the formula:

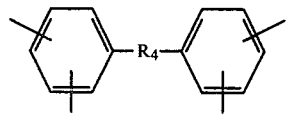

and wherein $R_4$ is $CF_3$-C-$CF_3$.

2. An aromatic bis (amino imide) having the formula:

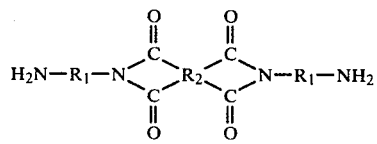

wherein $R_1$ is phenylene and $R_2$ is a tetravalent aryl radical having the formula:

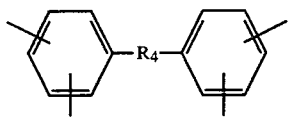

and wherein $R_4$ is $CF_3\text{-}C\text{-}CF_3$.

3. A method of curing a polyepoxide which comprises admixing a polyepoxide and an aromatic bis (amino-imide) as claimed in claim 1.

4. A cured polyepoxide produced by the process of claim 3.

5. In a composite material comprising carbon fibers imbedded in a matrix of a cured epoxy resin, the improvement wherein the epoxy resin is cured with an aromatic bis (amino-imide) as claimed in claim 1.